United States Patent [19]

Gosling et al.

[11] Patent Number: 5,401,893
[45] Date of Patent: Mar. 28, 1995

[54] COMBINATION DEHYDROCYCLODIMERIZATION AND DEHYDROGENATION PROCESS FOR PRODUCING AROMATIC AND OLEFIN PRODUCTS

[75] Inventors: Christopher D. Gosling, Roselle; Joseph H. Gregor, Itasca; Charles P. Luebke, Mt. Prospect, all of Ill.

[73] Assignee: UOP, Des Plaines, Ill.

[21] Appl. No.: 167,299

[22] Filed: Dec. 16, 1993

[51] Int. Cl.$^6$ .......................... C07C 5/00; C07C 2/00; C07C 6/00; C10G 35/06
[52] U.S. Cl. ..................... 585/322; 585/314; 585/316; 208/65; 208/138
[58] Field of Search .............. 585/314, 316, 322, 654, 585/659, 529, 417, 419; 208/65, 138

[56] References Cited
U.S. PATENT DOCUMENTS

| | | | |
|---|---|---|---|
| 4,447,653 | 5/1984 | Vora | 568/697 |
| 4,654,455 | 3/1987 | Chao | 585/415 |
| 4,724,271 | 2/1988 | Martindale et al. | 585/415 |
| 4,746,763 | 5/1988 | Kocal | 585/417 |
| 4,868,342 | 9/1989 | Verson | 568/697 |

Primary Examiner—Helen M. S. Sneed
Assistant Examiner—Bekir L. Yildirim
Attorney, Agent, or Firm—Thomas K. McBride; Eugene I. Snyder; Frank S. Molinaro

[57] ABSTRACT

This invention deals with a process for converting aliphatic $C_2$–$C_6$ hydrocarbons into $C_6^+$ aromatics and $C_3^=$/$C_4^=$ olefins. The process involves combining dehydrocyclodimerization (DHCD) with dehydrogenation. Thus, the feedstream is first sent to a DHCD zone which produces an effluent stream which contains $C_6^+$ aromatics along with $C_1$–$C_5$ hydrocarbons. This effluent stream is separated into a stream containing $C_1$–$C_4$ hydrocarbons and one containing $C_6^+$ aromatics. The $C_1$–$C_4$ containing stream is flowed to a dehydrogenation zone to produce $C_3^=$/$C_4^=$ olefins.

10 Claims, 1 Drawing Sheet

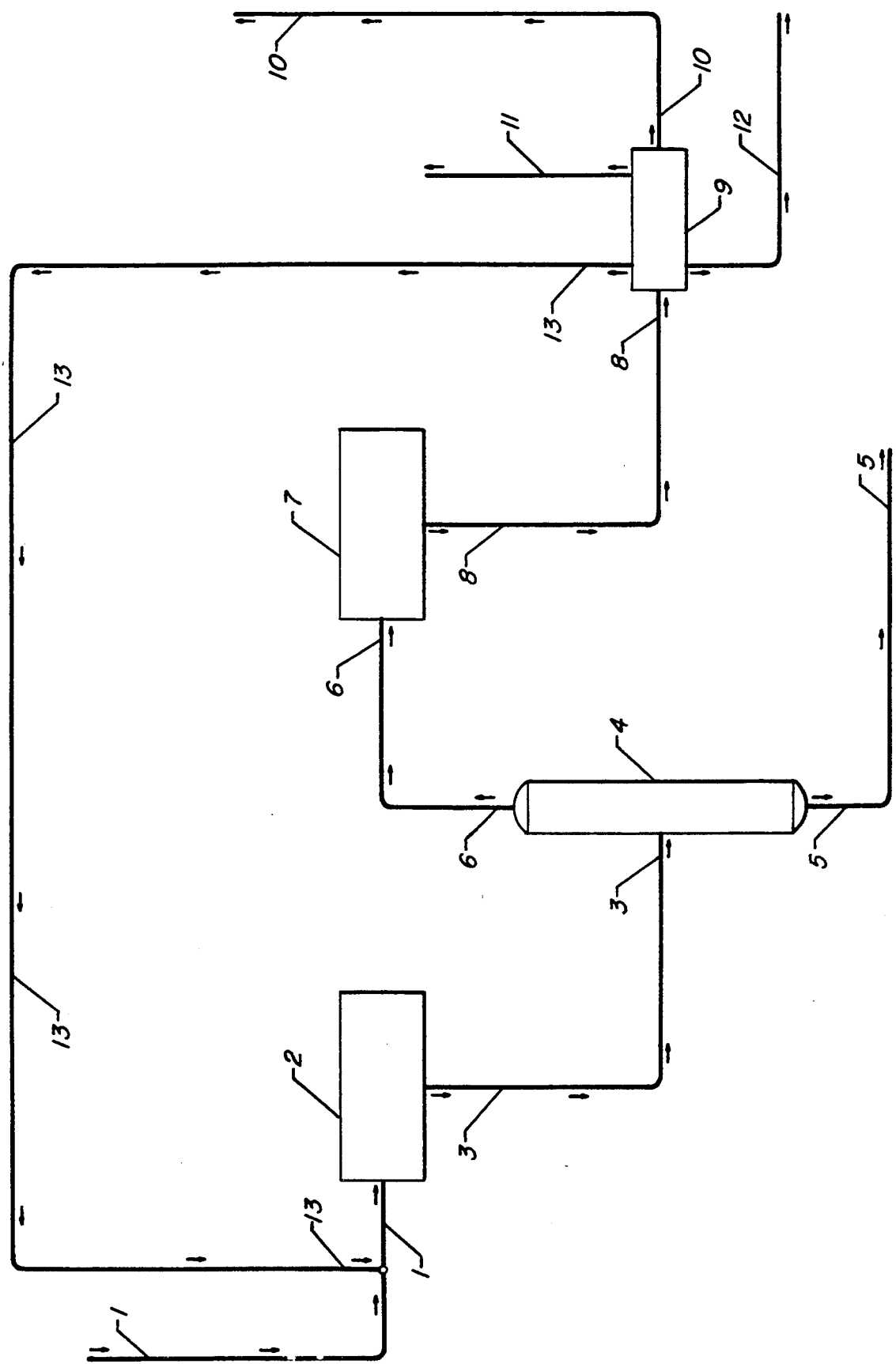

COMBINATION DEHYDROCYCLODIMERIZATION AND DEHYDROGENATION PROCESS FOR PRODUCING AROMATIC AND OLEFIN PRODUCTS

FIELD OF THE INVENTION

This invention relates to a hydrocarbon conversion process. Specifically, a light aliphatic hydrocarbon is first converted to aromatics plus hydrogen. The hydrogen and unconverted hydrocarbons are next flowed to a dehydrogenation zone where the hydrocarbons are converted to olefins.

BACKGROUND OF THE INVENTION

Dehydrocyclodimerization (DHCD) is a process in which aliphatic hydrocarbons containing from 2 to 6 carbon atoms per molecule are reacted over a catalyst to produce a high yield of aromatics and hydrogen. This process is well known and is described in detail in U.S. Pat. Nos. 4,654,455 and 4,746,763 which are incorporated by reference. Typically, the dehydrocyclodimerization reaction is carried out at temperatures in excess of 500° C., using dual functional catalysts containing acidic and dehydrogenation components. The acidic function is usually provided by a zeolite which promotes the oligomerization and aromatization reactions, while a non-noble metal component promotes the dehydrogenation function.

Since the product stream from the dehydrocyclodimerization process contains a mixture of compounds, it must undergo several separation steps in order to obtain usable products. An initial fractionation will separate the $C_6^+$ products from uncondensed materials which include fuel gas, hydrogen and unreacted hydrocarbons. The uncondensed material is compressed and sent to a gas recovery section where hydrogen and fuel gas are separated from the unconverted hydrocarbons which are recycled to the dehydrocyclodimerization zone.

Significant fixed and operating costs are associated with the product compressor and gas recovery equipment. The high compression ratio required to condense the materials accounts for the substantial capital and operating costs. Therefore, it would be desirable to eliminate the high costs associated with the compressor and gas recovery equipment.

Applicants have found a solution to this problem which involves dehydrogenation. The uncondensed materials from the product fractionator are flowed to a dehydrogenation zone where the unreacted hydrocarbons ($C_3/C_4$) are converted to olefins. Since the operating pressure of the dehydrogenation zone is lower than that of the DHCD zone, there is no need for a compressor. The effluent stream from the dehydrogenation zone is separated into a hydrogen stream, a $C_1/C_2$ fuel gas stream, a $C_3^=/C_4^=$ olefin stream and an unreacted hydrocarbon stream (compression is required for this separation). The unreacted stream is recycled to the DHCD zone, while the olefin stream is collected and the other streams are vented.

SUMMARY OF THE INVENTION

As stated, the present invention relates to a process for converting $C_2-C_6$ aliphatic hydrocarbons to aromatics and $C_3^=/C_4^=$ olefins. Accordingly, one embodiment of the invention is a process for producing aromatic and olefinic hydrocarbons comprising:

a) flowing a hydrocarbon feedstream containing $C_2-C_6$ aliphatic hydrocarbons into a dehydrocyclodimerization zone where said feedstream is contacted with a bed of solid dehydrocyclodimerization catalyst at dehydrocyclodimerization conditions, thereby producing an effluent stream containing $C_6^+$ aromatics, hydrogen and $C_1-C_4$ aliphatic hydrocarbons;

b) flowing the effluent stream to a first separation zone operated at conditions effective to provide a first bottoms stream containing $C_6^+$ aromatics and a first overhead stream containing hydrogen and $C_1-C_4$ aliphatic hydrocarbons;

c) flowing the first overhead stream to a dehydrogenation zone where the stream is contacted with a dehydrogenation catalyst in the presence of hydrogen at dehydrogenation conditions, thereby producing a second effluent stream containing $C_3^=/C_4^=$, hydrogen and unreacted $C_1-C_4$ aliphatic hydrocarbons;

d) flowing the second effluent stream to a gas recovery zone operated at conditions to separate the second effluent stream into a hydrogen stream, a fuel gas ($C_1/C_2$) stream, a $C_3^=/C_4^=$ and a $C_3-C_4$ aliphatic recycle stream;

e) recycling the $C_3-C_4$ aliphatic stream to the dehydrocyclodimerization zone of step (a).

This and other objects and embodiments of this invention will become more apparent after a detailed description of the invention.

BRIEF DESCRIPTION OF THE DRAWING

The FIGURE is a simplified process flow diagram of one embodiment of the invention showing the formation of aromatic and olefinic ($C_3^=/C_4^=$) hydrocarbons from a $C_2-C_6$ aliphatic hydrocarbon stream.

DETAILED DESCRIPTION OF THE INVENTION

As stated, this invention relates to a process for preparing both aromatic and light olefinic ($C_3^=/C_4^=$) hydrocarbons from a light aliphatic hydrocarbon stream. The process uses a dehydrocyclodimerization zone and a dehydrogenation zone. The feedstream to the present process contains light aliphatic hydrocarbons having from 2 to 6 carbon atoms per molecule. The feedstream may contain a single compound or a mixture of two or more of these compounds. Preferred compounds are propane and butanes. It is also preferred that the concentration of $C_5$ and $C_6$ hydrocarbons in the feedstream be held to a practical level, preferably below 20 mole percent.

Regardless of the composition of the feedstream, the feedstream is flowed into a dehydrocyclodimerization (DHCD) zone which converts a significant portion of the aliphatic feedstream into aromatic hydrocarbons, i.e., $C_6^+$ aromatics. The majority of the $C_6^+$ product hydrocarbons are benzene, toluene and the various xylene isomers with a small amount (about 8%) of $C_9^+$ aromatics. Hydrogen is also a product of the process. Since conversion of the aliphatic feedstream to aromatic products is not one hundred percent, the product effluent stream will also contain unreacted feedstock along with $C_1/C_2$ hydrocarbons. The configuration of the reaction zone and the composition of the catalyst employed in the reaction zone are well known in the art and are described here for completeness.

Usually the reaction zone consists of a moving bed radial flow multistage reactor as described, for example, in U.S. Pat. Nos. 4,110,081 and 4,403,909 which are incorporated by reference. These patents also describe catalyst regeneration systems and various aspects of moving catalyst bed operations and equipment. A preferred moving bed reactor system employs a spherical catalyst having a diameter between about 0.4 millimeters and 3.2 millimeters. The catalyst preferably comprises a zeolitic material, a metallic component and a binder. U.S. Pat. Nos. 4,654,455, 4,746,763 and 5,169,812, which are incorporated by reference, describe DHCD catalysts and methods of preparing them. A brief description of these catalysts will be presented.

The zeolites which may be used are any of those which have a Si:Al ratio greater than about 10 and preferably greater than 20 and a pore diameter of about 5 to 6 Angstroms. Specific examples of zeolites which can be used are the ZSM family of zeolites. Included among this ZSM family are ZSM-5, ZSM-8, ZSM-11, ZSM-12 and ZSM-35. The preparation of these ZSM-type zeolites is well known in the art and generally are prepared by crystallizing a mixture containing an alumina source, a silica source, an alkali metal source, water and a tetraalkyl ammonium compound or its precursor. The amount of zeolite present in the catalyst can vary considerably but usually is present in an amount from about 30 to about 90 weight percent and preferably from about 50 to about 70 weight percent of the catalyst.

A second component of these catalysts is a phosphorus containing alumina (hereinafter referred to as aluminum phosphate) component. The phosphorus may be incorporated with the alumina in any acceptable manner known in the art. One preferred method of preparing this aluminum phosphate is that described in U.S. Pat. No. 4,629,717 which is incorporated by reference. The technique described in the '717 patent involves the gellation of a hydrosol of alumina which contains a phosphorus compound using the well-known oil drop method. Generally this technique involves preparing a hydrosol by digesting aluminum in aqueous hydrochloric acid at reflux temperatures of about 80° to 105° C. The ratio of aluminum to chloride in the sol ranges from about 0.7:1 to about 1.5:1 weight ratio. A phosphorus compound is now added to the sol. Preferred phosphorus compounds are phosphoric acid, phosphorous acid and ammonium phosphate. The relative amount of phosphorus and aluminum expressed in molar ratios ranges from about 1:1 to 1:100 on an elemental basis.

The resulting aluminum phosphate hydrosol mixture is now gelled. One method of gelling this mixture involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 93° C. to about 149° C. (200°–300° F.) and subjected to a calcination procedure at a temperature of about 450° C. to about 703° C. (850°–1300° F.) for a period of about 1 to about 20 hours. The amount of phosphorus containing alumina component present (as the oxide) in the catalyst can range from about 10 to about 70 weight percent and preferably from about 30 to about 50 weight percent.

The zeolite and aluminum phosphate binder are mixed and formed into particles by means well known in the art such as gellation, pilling, nodulizing, marumerizing, spray drying, extrusion or any combination of these techniques. A preferred method of preparing the zeolite/aluminum phosphate support involves adding the zeolite either to an alumina sol or a phosphorus compound, forming a mixture of the alumina sol/-zeolite/phosphorus compound which is now formed into particles by employing the oil drop method described above. The particles are calcined as described above to give a support.

Another component of these catalysts is a gallium component. The gallium component may be deposited onto the support in any suitable manner known to the art which results in a uniform dispersion of the gallium. Usually the gallium is deposited onto the support by impregnating the support with a salt of the gallium metal. The particles are impregnated with a gallium salt selected from the group consisting of gallium nitrate, gallium chloride, gallium bromide, gallium hydroxide, gallium acetate, etc. The amount of gallium which is deposited onto the support varies from about 0.1 to about 5 weight percent of the finished catalyst expressed as the metal.

The gallium compound may be impregnated onto the support particles by any technique well known in the art such as dipping the catalyst into a solution of the metal compounds or spraying the solution onto the support. One preferred method of preparation involves the use of a steam jacketed rotary dryer. The support particles are immersed in the impregnating solution contained in the dryer and the support particles are tumbled therein by the rotating motion of the dryer. Evaporation of the solution in contact with the tumbling support is expedited by applying steam to the dryer jacket. After the particles are completely dry, they are heated under a hydrogen atmosphere at a temperature of about 500 to about 700° C. for a time of about 1 to about 15 hours. Although a pure hydrogen atmosphere is preferred to reduce and disperse the gallium, the hydrogen may be diluted with nitrogen. Alternatively, it is envisioned that the reduction and dispersion can be done in situ in the actual reactor vessel used for dehydrocyclodimerization by using either pure hydrogen or a mixture of hydrogen and hydrocarbons. Next the hydrogen treated particles are heated in air and steam at a temperature of about 400° to about 700° C. for a time of about 1 to about 10 hours. The amount of steam present in the air varies from about 1 to about 40 percent.

A particularly preferred catalyst is one described in U.S. Pat. No. 5,169,812. This reference describes a gallium/aluminum phosphate/zeolite catalyst which has been treated with an aqueous solution of a weakly acidic ammonium salt or a dilute acid solution, e.g., ammonium chloride or hydrochloric acid.

The dehydrocyclodimerization conditions which are employed in the reaction zone will vary depending on such factors as feedstock composition and desired conversion. A desired range of conditions for the dehydrocyclodimerization of $C_2-C_6$ aliphatic hydrocarbons to aromatics include a temperature from about 350° C. to about 650° C., a pressure from about 100 kPa to about 2,020 kPa and a liquid hourly space velocity from about 0.2 to about 5 hrs$^{-1}$. The preferred process conditions are a temperature in the range from about 400° to about 550° C., a pressure in the range from about 200 to about 1,015 kPa and a liquid hourly space velocity of between 1.0 to 4.0 hrs$^{-1}$. It is understood that as the average carbon number of the feedstream increases, a temperature in the lower end of the temperature range is required for optimum performance and conversely as the average carbon number of the feed decreases, the higher the required temperature.

The effluent stream from the DHCD zone which contains $C_6^+$ aromatics, hydrogen, unreacted feed and $C_1/C_2$ is separated into a stream containing $C_6=$ aromatics and one containing the other components. The stream containing hydrogen, unreacted feedstock and $C_1/C_2$ hydrocarbons is now fed to a dehydrogenation zone. Dehydrogenation reactions zones are well known in the art as exemplified by U.S. Pat. Nos. 4,447,653 and 4,868,342 which are incorporated by reference. The dehydrogenation zone like the DHCD zone comprises at least one radial flow reactor. The dehydrogenation reaction is a highly endothermic reaction which is typically effected at low (near atmospheric) pressure conditions. The precise dehydrogenation temperature and pressure employed in the dehydrogenation reaction zone will depend on a variety of factors such as the composition of the paraffinic hydrocarbon feedstock, the activity of the selected catalyst, and the hydrocarbon conversion rate. In general, dehydrogenation conditions include a pressure of from about 0 to about 3,500 kPa and a temperature of from about 480° C. (900° F.) to about 760° C. (1400° F.). The hydrocarbons are charged to the reaction zone and contacted with the catalyst contained therein at a liquid hourly space velocity of from about 1 to about 10. Hydrogen is suitably admixed with the hydrocarbon feedstock in a mole ratio of from about 0.1 to about 10. Preferred dehydrogenation conditions, particularly with respect to $C_3-C_4$ paraffinic hydrocarbon feedstocks, include a pressure of from about 0 to about 2,000 kPa and a temperature of from about 540° C. (1000° F.) to about 705° C. (1300° F.), a liquid hourly space velocity of from about 1 to about 5 hr$^{-1}$, and a hydrogen/hydrocarbon mole ratio of about 0.5 to about 2.

The dehydrogenation zone of this invention may use any suitable dehydrogenation catalyst. Generally, the preferred catalyst comprises a platinum group metal, an alkali metal component, and a porous inorganic carder material. The catalyst may also contain one or more modifier metal which advantageously improve the performance of the catalyst. It is preferable that the porous carrier material of the dehydrogenation catalyst be an absorptive high surface area support having a surface area of about 25 to about 500 m$^2$/g. The porous carrier material should be relatively refractory to the conditions utilized in the reaction zone and may be chosen from those carrier materials which have traditionally been utilized in dual function hydrocarbon conversion catalysts. A porous carrier material may, therefore, be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxides such as alumina, titanium dioxide, zirconium dioxides, magnesia, silica alumina, alumina boria, etc. or a combination of one or more of these materials. The preferred porous carder material is a refractory inorganic oxide, with the best results being obtained with an alumina carrier material. The aluminas, such as gamma alumina, give the best results in general. The preferred catalyst will have a gamma alumina carrier which is in the form of spherical particles having relatively small diameters on the order of about 1/16 inch.

The preferred dehydrogenation catalyst also contains a platinum group metal. Of the platinum group metals, which include palladium, rhodium, ruthenium, osmium and iridium, the use of platinum is preferred. The platinum group metal may exist within the final catalyst composite as a compound such as an oxide, sulfide, halide, oxysulfide, etc., or an elemental metal or in combination with one or more other ingredients of the catalyst. It is believed that the best results are obtained when substantially all the platinum group metal exists in the elemental state. The platinum group metal generally comprises from about 0.01 to about 2 wt. % of the final catalytic composite, calculated on an elemental basis. It is preferred that the platinum content of the catalyst be between about 0.1 and 1 wt. %. The preferred platinum group metal is platinum, with palladium being the next preferred metal. The platinum group metal may be incorporated into the catalyst composite in any suitable manner such as by coprecipitation or coagulation with the preferred carder material, or by ion exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinic or chloropalladic acid. An acid such as hydrogen chloride is generally added to the impregnation solution to aid in the distribution of the platinum group component throughout the carder material.

Additionally, the preferred catalyst contains an alkali metal component chosen from cesium, rubidium, potassium, sodium and lithium. The preferred alkali metal is normally either potassium or lithium, depending on the feed hydrocarbon. The concentration of the alkali metal may range from about 0.1 to 5 wt. %, but is preferably between 1 and about 4 wt. % calculated on an elemental basis. This component may be added to the catalyst by the methods described above as a separate step or simultaneously with the solution of another component. With some alkali metals, it may be necessary to limit the halogen content to less than 0.5 wt. % and preferably less than 0.1 wt. %, while others may have higher halogen content.

As noted previously, the dehydrogenation catalyst may also contain a modifier metal. One such preferred promoter metal is tin. The tin component should constitute about 0.01 to about 1 wt. % tin. It is preferred that the atomic ratio of tin to platinum be between 1:1 and about 6:1. The tin component may be incorporated into the catalytic composite in any suitable manner known to effectively disperse this component onto the carrier material.

The FIGURE illustrates one embodiment of the invention. Those skilled in the art will recognize that this process flow diagram has been simplified by the elimination of many pieces of process equipment including heat exchangers, process control systems, pumps, fractionation column overhead and reboiler systems, etc. which are not necessary to an understanding of the process. It may also be readily discerned that the process flow presented in the drawings may be modified in many aspects without departing from the basis overall concept of the invention. Referring now to the FIGURE, a feedstream of $C_2$-$C_6$ hydrocarbons and preferably $C_3$-$C_4$ is flowed via line 1 into reaction zone 2. As stated, reaction zone 2 is a dehydrocyclodimerization (DHCD) zone where the $C_2$-$C_6$ hydrocarbon feedstream is contacted with a solid catalyst under DHCD conditions. The effluent stream, which contains $C_6^+$ aromatics, hydrogen, $C_1/C_2$ and unreacted feedstock, is removed via line 3 and flowed to separation zone 4.

Separation zone 4 is operated at conditions sufficient to separate the effluent stream into a first bottoms stream containing $C_5^+$ hydrocarbons and a first overhead stream containing hydrogen and $C_1$-$C_4$ aliphatic hydrocarbons. The first bottoms stream contains aromatic and a small amount of non-aromatic hydrocarbons, ($C_5^+$), with the majority of the stream composed of $C_6^+$ aromatics, especially benzene, toluene and xylenes. The first bottoms stream is removed via line 5 and is either collected as is or is further processed to separate the $C_6^+$ aromatics into benzene, toluene and xylenes products.

The first overhead stream is removed from zone 4 via line 6 and flowed to dehydrogenation zone 7. In zone 7 the stream is contacted with a dehydrogenation catalyst which converts the $C_3/C_4$ saturated hydrocarbons to olefins ($C_3^=/C_4^=$). This second effluent stream is removed via fine 8 and flowed to gas recovery zone 9. This zone is operated at conditions to separate the components of the second effluent stream into a hydrogen stream which is removed via line 10, a fuel gas ($C_1/C_2$) stream which is removed via line 11, a $C_3^=/C_4^=$ product stream which is removed via line 12 and a $C_3$-$C_4$ recycle aliphatic stream which is removed via line 13. The aliphatic stream is flowed into line 1 and recycled into DHCD zone 2. A compressor is required as part of zone 9 in order to effectively separate the various components.

As stated, the instant process presents several advantages over the art. First, capital costs are significantly reduced owing to the fact that compression of the product stream from the dehydrocyclodimerization zone is not necessary. Second, the instant process can provide the total feedstock requirements for a downstream aromatics derivate application. Finally, optimal feedstock utilization is obtained by elimination of separation inefficiencies.

We claim as our invention:

1. A process for producing aromatic and olefinic hydrocarbons comprising:

a) flowing a hydrocarbon feedstream containing $C_2$-$C_6$ aliphatic hydrocarbons into a dehydrocyclodimerization zone where said feedstream is contacted with a bed of a solid dehydrocyclodimerization catalyst at dehydrocyclodimerization conditions, thereby producing an effluent stream containing $C_6^+$ aromatics, hydrogen and $C_1$-$C_4$ aliphatic hydrocarbons;

b) flowing the effluent stream to a first separation zone and separating the stream to obtain a first bottoms stream containing $C_6^+$ aromatics and a first overhead stream containing hydrogen and $C_1$-$C_4$ aliphatic hydrocarbons;

c) flowing the first overhead stream to a dehydrogenation zone and contacting said steam with a dehydrogenation catalyst in the presence of hydrogen at dehydrogenation conditions, thereby producing a second effluent stream containing $C_3^=/C_4^=$ olefins, hydrogen and unreacted $C_1$-$C_4$ aliphatic hydrocarbons;

d) flowing the second effluent stream to a gas recovery zone and separating the second effluent stream into a hydrogen stream, a fuel gas ($C_1/C_2$) stream, a $C_3^=/C_4^=$ olefins and a $C_3$-$C_4$ recycle aliphatic stream;

e) recycling the $C_3$-$C_4$ aliphatic stream to the dehydrocyclodimerization zone of step (a).

2. The process of claim 1 where the dehydrocyclodimerization conditions include a temperature of about 350° C. to about 650° C., a pressure of about 100 kPa to about 2,020 kPa and a liquid hourly space velocity of about 0.2 to about 5 $hr^{-1}$.

3. The process of claim 1 where the dehydrocyclodimerization catalyst comprises a zeolite component, a gallium component and an aluminum phosphate binder.

4. The process of claim 1 where the dehydrogenation conditions include a temperature of about 480° C. to about 760° C., a pressure of about 0 to about 3,500 kPa, a liquid hourly space velocity of about 1 to about 5 $hr^{-1}$ and a hydrogen to hydrocarbon ratio of about 0.1 to about 10.

5. The process of claim 1 where the dehydrogenation catalyst comprises a platinum group metal dispersed on a porous inorganic carrier material.

6. The process of claim 5 where the platinum group metal is platinum and is present in an amount from about 0.01 to about 2 weight percent of the catalyst.

7. The process of claim 5 further characterized in that the dehydrogenation catalyst contains an alkali metal component.

8. The process of claim 7 where the alkali metal component is potassium.

9. The process of claim 5 further characterized in that the dehydrogenation catalyst contains a modifier metal.

10. The process of claim 9 where the modifier metal is tin.

* * * * *